United States Patent [19]

Nathan

[11] Patent Number: 5,330,516
[45] Date of Patent: Jul. 19, 1994

[54] DEVICE FOR GENERATING HAND FUNCTION

[75] Inventor: Roger H. Nathan, Beer Sheva, Israel

[73] Assignee: Ben-Gurion University of the Negev Research & Development Authority, Beer Sheva, Israel

[21] Appl. No.: 859,101

[22] Filed: Mar. 27, 1992

[30] Foreign Application Priority Data

Mar. 28, 1991 [IL] Israel .................................. 97701

[51] Int. Cl.$^5$ .............................................. A61N 1/36
[52] U.S. Cl. .................................... 607/48; 607/149
[58] Field of Search .................... 602/2, 5; 128/419 R, 128/385

[56] References Cited

U.S. PATENT DOCUMENTS

| | | | |
|---|---|---|---|
| 1,635,230 | 7/1927 | Spicer | 602/5 |
| 3,911,910 | 10/1975 | Oesau | 128/419 R |
| 4,580,569 | 4/1986 | Petrofsky | 128/420 A |
| 4,697,808 | 10/1987 | Larson et al. | 272/70 |

FOREIGN PATENT DOCUMENTS 0557875 3/1987 Australia .

0302148 2/1989 European Pat. Off. .

Primary Examiner—William E. Kamm
Assistant Examiner—Scott M. Getzow
Attorney, Agent, or Firm—Jacobson, Price, Holman & Stern

[57] ABSTRACT

A device for generating hand function, having an S-type splint consisting of a forearm portion extending along the palmar side of the forearm, a palmo-dorsal transition portion leading to a dorsal portion extending across the dorsal side of the carpal bones of the hand, and a palmar portion, at least the end of which touches the palm of the hand of the wearer of the device at least indirectly, and a plurality of electrodes, at least indirectly mounted on the splint in positions in which they can make contact with skin portions directly overlying muscles to be stimulated. The electrodes are connectable to an electronic circuit adapted to produce, upon activation, stimulation currents delivered via combinations of the electrodes in predetermined, timed sequences to preselected groups of muscles. At least one switch is actuatable by the wearer of the device, by which switch the predetermined, timed sequences can be initiated.

15 Claims, 6 Drawing Sheets

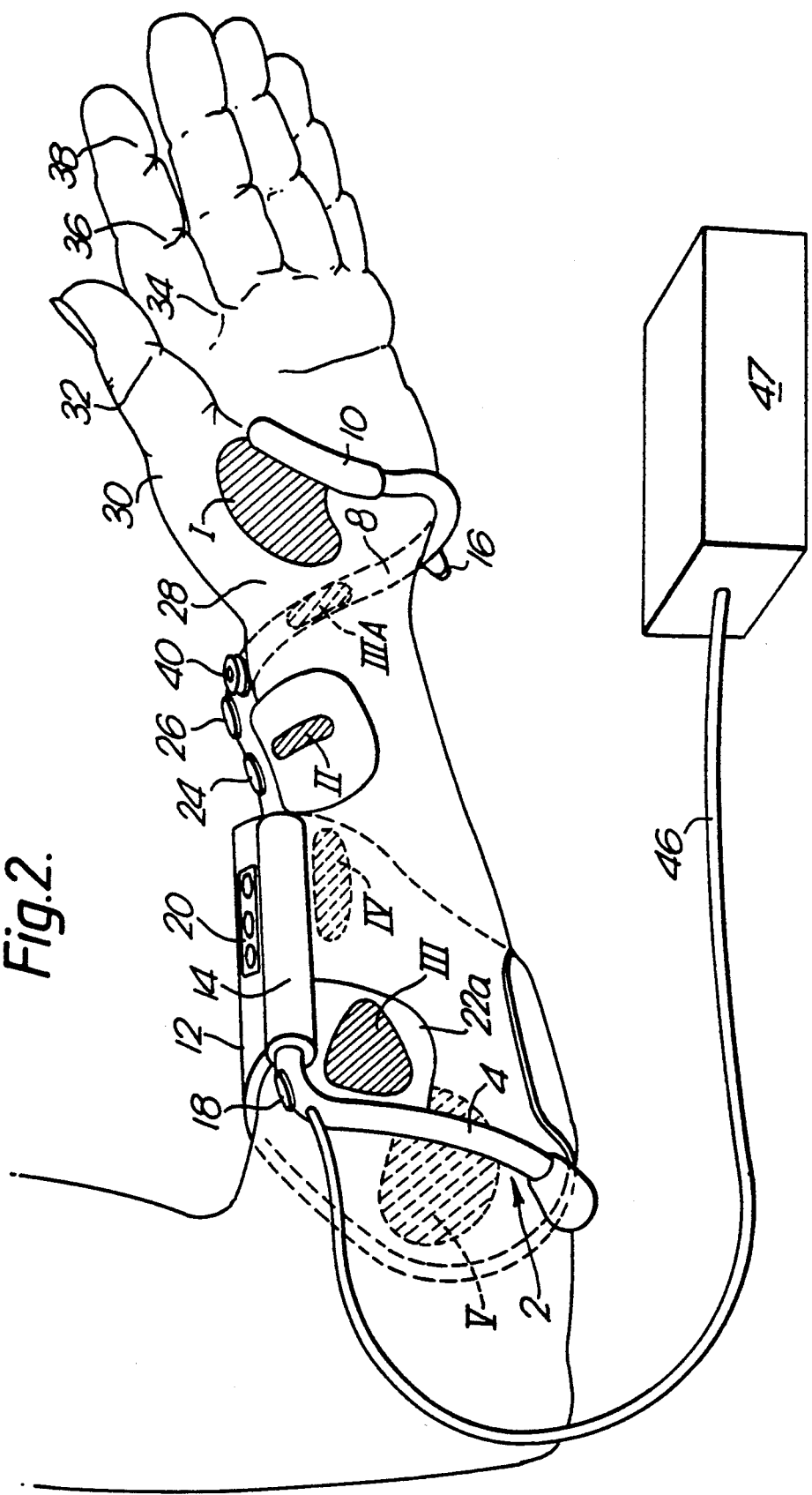

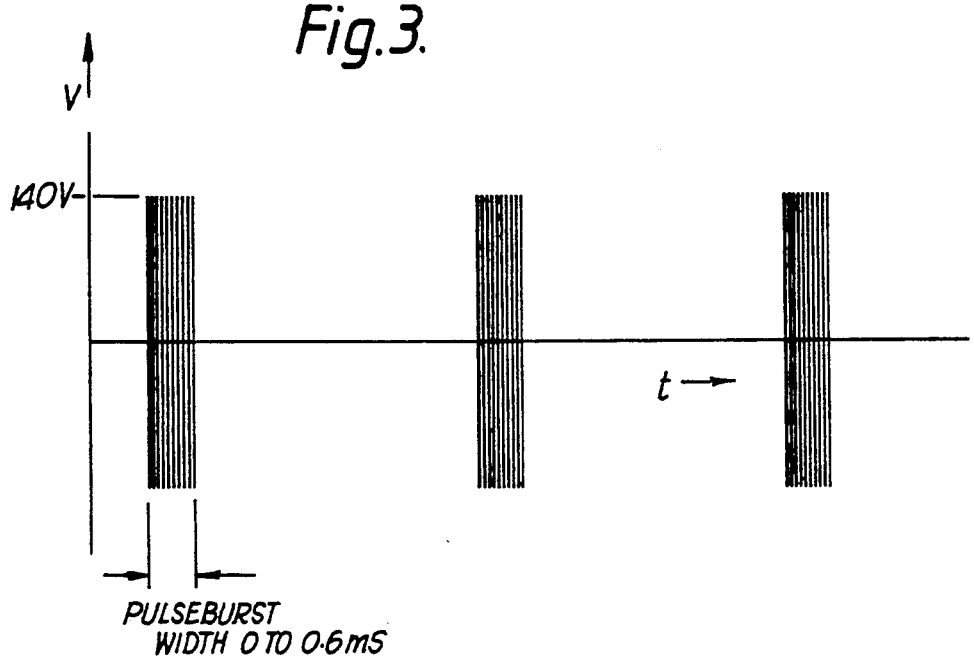
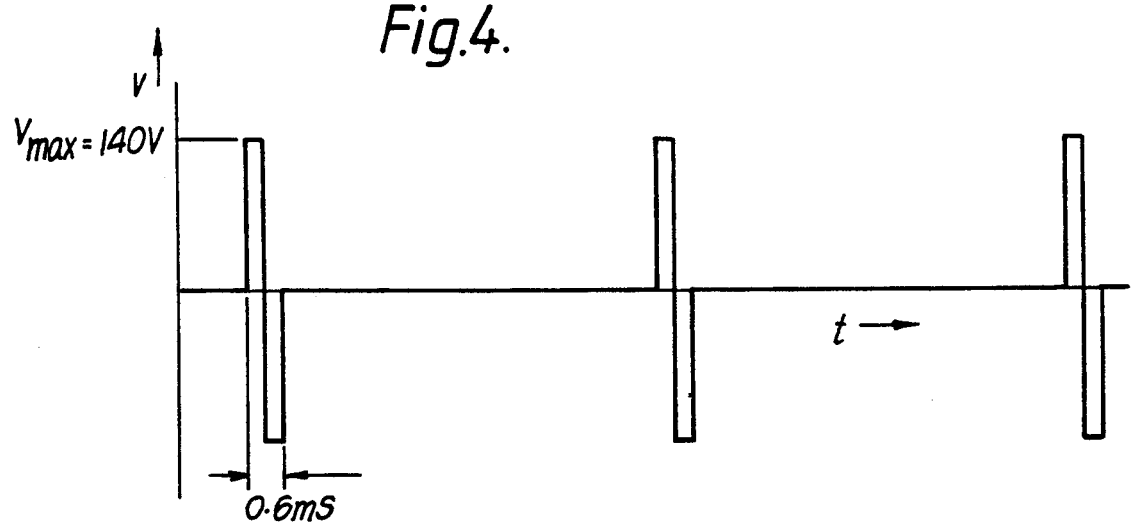

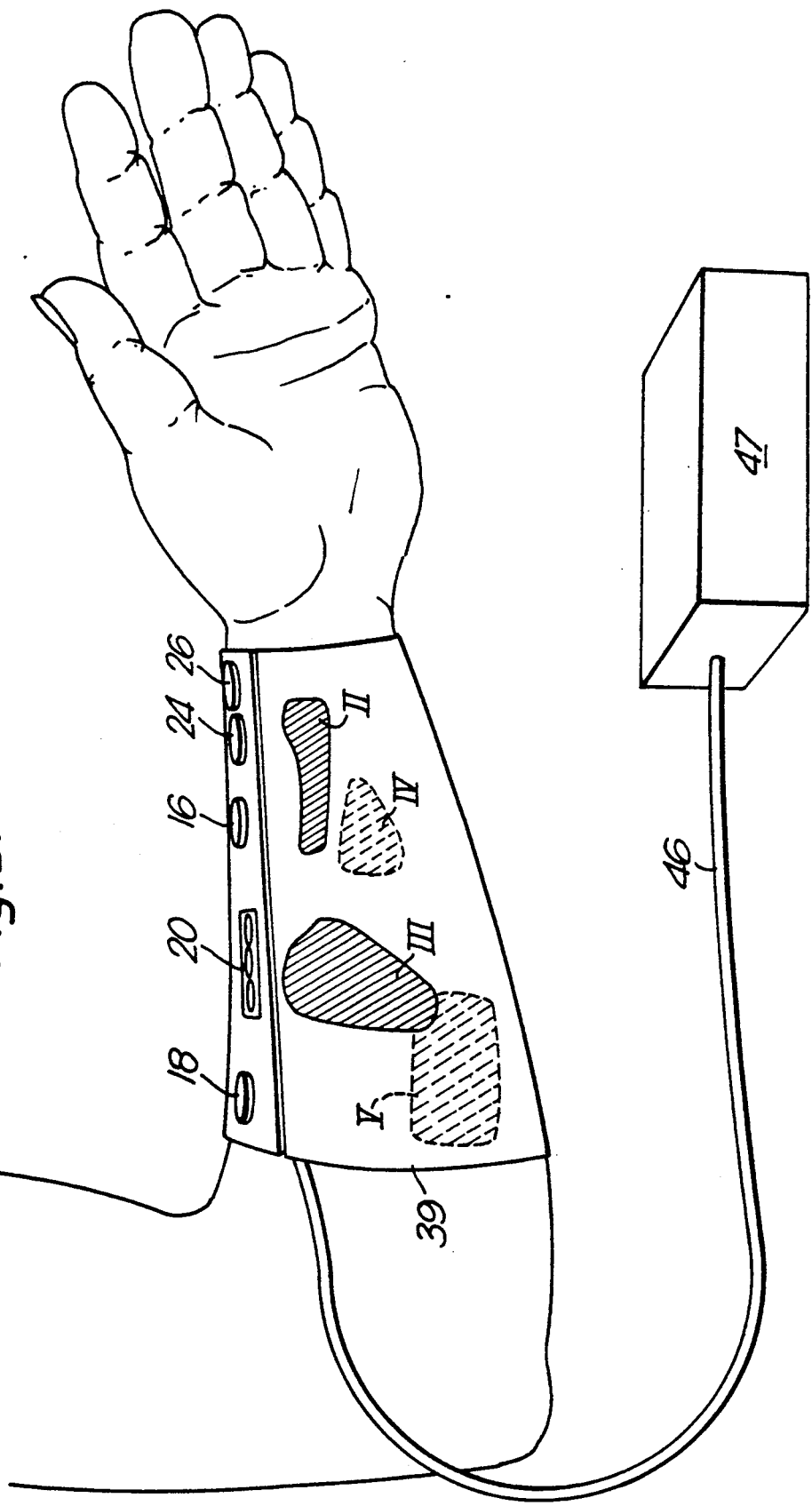

DEVICE FOR GENERATING HAND FUNCTION

The present invention relates to a device for generating hand function.

Paralysis of the muscles of the hand may be caused by a break in the lines of communication between the central nervous system and the muscles. This may be due, for example, to a spinal lesion at above C7 level, or to other diseases or injury to the nervous system. Electrical stimulation can cause the muscles to contract, and systems based on electrical stimulation have been used for the restoration of functional movements to parts of the human body.

Systems specifically designed for restoring hand function may be external or implanted. External systems have several problems preventing their widespread use outside of the specialized clinic. The muscles controlling hand function are small and cannot be activated individually by standard stimulating electrodes due to low resolution of the stimulation field. A whole group of muscles is activated when the forearm is stimulated by the standard electrode.

A further problem in the use of external stimulation systems, especially those applied to the upper limb, has been the difficulty for the patient or his attendant of placing the system on the arm., i.e., of "donning" the system. This has required considerable time and expertise on the part of the attendant; no system has been available which allows the patient to don the system on his own. The dependence of the patient on the patience and expertise of the attendant has been another factor limiting home use of a stimulation system for the hand. The time and expertise required to don the system, and the unnatural hand configurations generated by standard electrodes, have resulted in little or no long-term home use of external upper-limb stimulation systems for hand function.

Petrofsky (U.S. Pat. No. 4,580,569) addresses the problem of the activation of deep-lying muscles of the forearm by the use of interferential stimulation currents. Donning and doffing of the system has to be carried out by an attendant and cannot be achieved by the quadriplegic himself. A shoulder sensor for input commands is specified in Petrofsky's system. This a quadriplegic would be unable to don himself. A cuff with a zip fastener houses the electrodes. This, too, a quadriplegic would be unable to don himself. Finally, no specific location is given as to where to attach or house the controller. This is important if the quadriplegic is to don the system unaided. This system, therefore, is not designed to be donned and doffed quickly and unaided by the quadriplegic, but has to be placed in modular parts onto the body of the quadriplegic by his attendant.

Petrofsky also describes a different technique of locating the electrodes over the muscles. The cuff itself is located by tattoo marks on the skin surface. The skin tends to move with respect to the underlying musculature, particularly when the musculature is somewhat atrophied and when the arm is articulated, as in forearm pronation-supination.

The Petrofsky disclosure also suggests the use of standard electrodes (Medtronic Model 3795) which are relatively large and of inferior resolution which, when applied to hand and forearm musculature, are liable to produce unwanted overflow involving non-targeted muscles.

It is one of the objects of the present invention to overcome the disadvantages and drawbacks of the prior art devices and to provide a device for generating hand function that permits a patient with paralyzed hands and wrists not only to don and doff the device himself without undue effort, but also to adjust and operate it unaided, and that uses controlled-geometry electrodes, largely preventing undesirable overflow of stimulation pulses to adjacent, non-target muscles resulting in unnatural hand configurations; the electrodes contacting the forearm and hand segments effectively using for proper location the underlying bone structure of the forearm and the hand.

According to the invention, this is achieved by providing a device for generating hand function comprising an S-type splint consisting of a forearm portion extending along the palmar side of the forearm, a palmo-dorsal transition portion leading to a dorsal portion extending across the dorsal side of the carpal bones of the hand, and a palmar portion, at least the end of which touches the palm of the hand of the wearer of said device at least indirectly; a plurality of electrodes, at least indirectly mounted on said splint in positions in which they can make contact with skin portions directly overlying muscles to be stimulated, said electrodes being connectable to an electronic circuit adapted to produce, upon activation, stimulation currents delivered via combinations of said electrodes in predetermined, timed sequences to preselected groups of muscles; and at least one switching means actuatable by the wearer of said device, by which means said predetermined, timed sequences can be initiated.

The invention further provides a device for generating hand function, comprising a cuff donnable on, and substantially enveloping, the forearm; a plurality of electrodes at least indirectly mounted on said cuff in positions in which they can make contact with skin portions directly overlying muscles to be stimulated, said electrodes being connectable to an electronic circuit adapted to produce, upon activation, stimulation currents delivered via combinations of said electrodes in predetermined, timed sequences to preselected groups of muscles; and at least one switching means actuatable by the wearer of said device, by which means said predetermined, timed sequences can be initiated.

The invention will now be described in connection with certain preferred embodiments, with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent-to those skilled in the art how the several forms of the invention may be embodied in practice.

In the drawings:

FIG. 2 is a similar view of a second embodiment which facilitates voluntary or stimulated wrist flexion;

FIG. 3 illustrates a first type of stimulation pulses, arranged in bursts of a frequency of 18 Hz;

FIG. 4 shows another type of stimulation pulses, at the same frequency of 18 Hz;

FIG. 5 illustrates a forearm cuff not extending to the hand, for cases where adequate voluntary wrist extension is present;

Figure 8:
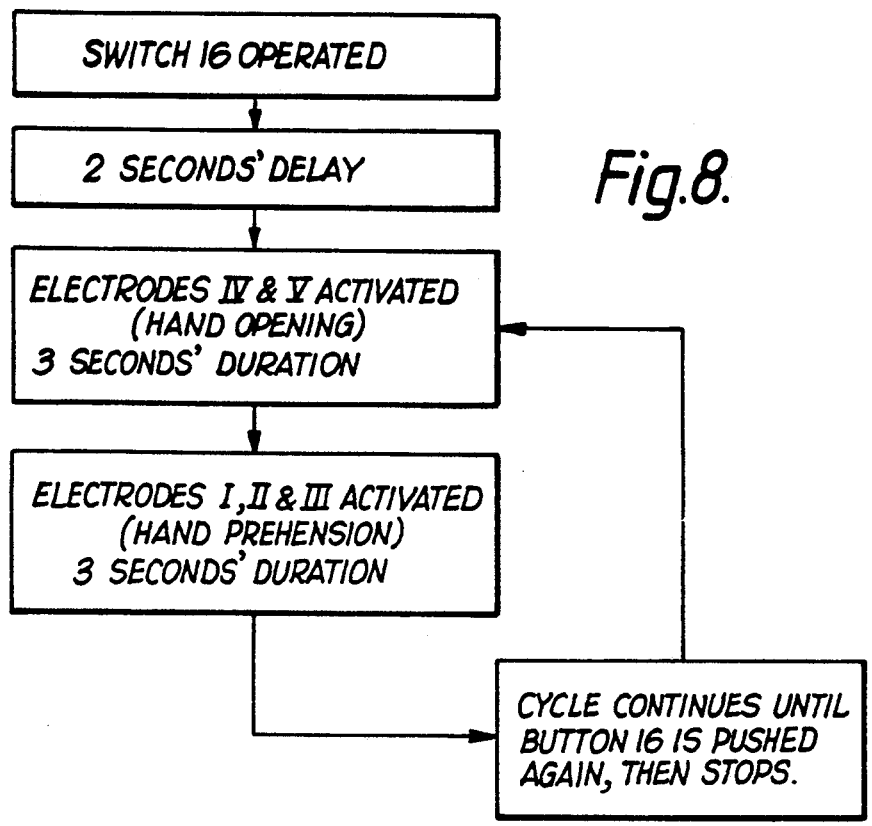

FIG. 8 gives the operational sequence in the physiotherapy mode, and

Figure 9:
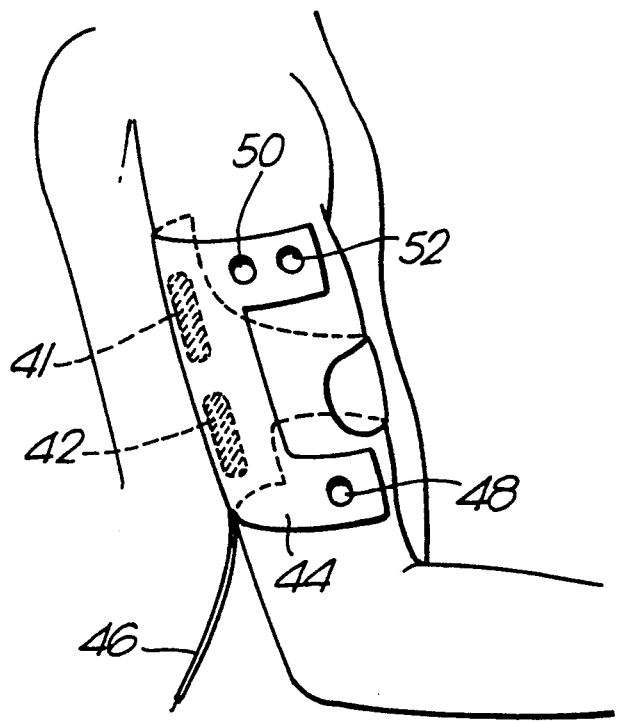

FIG. 9 represents an upper-arm cuff.

Figure 1:
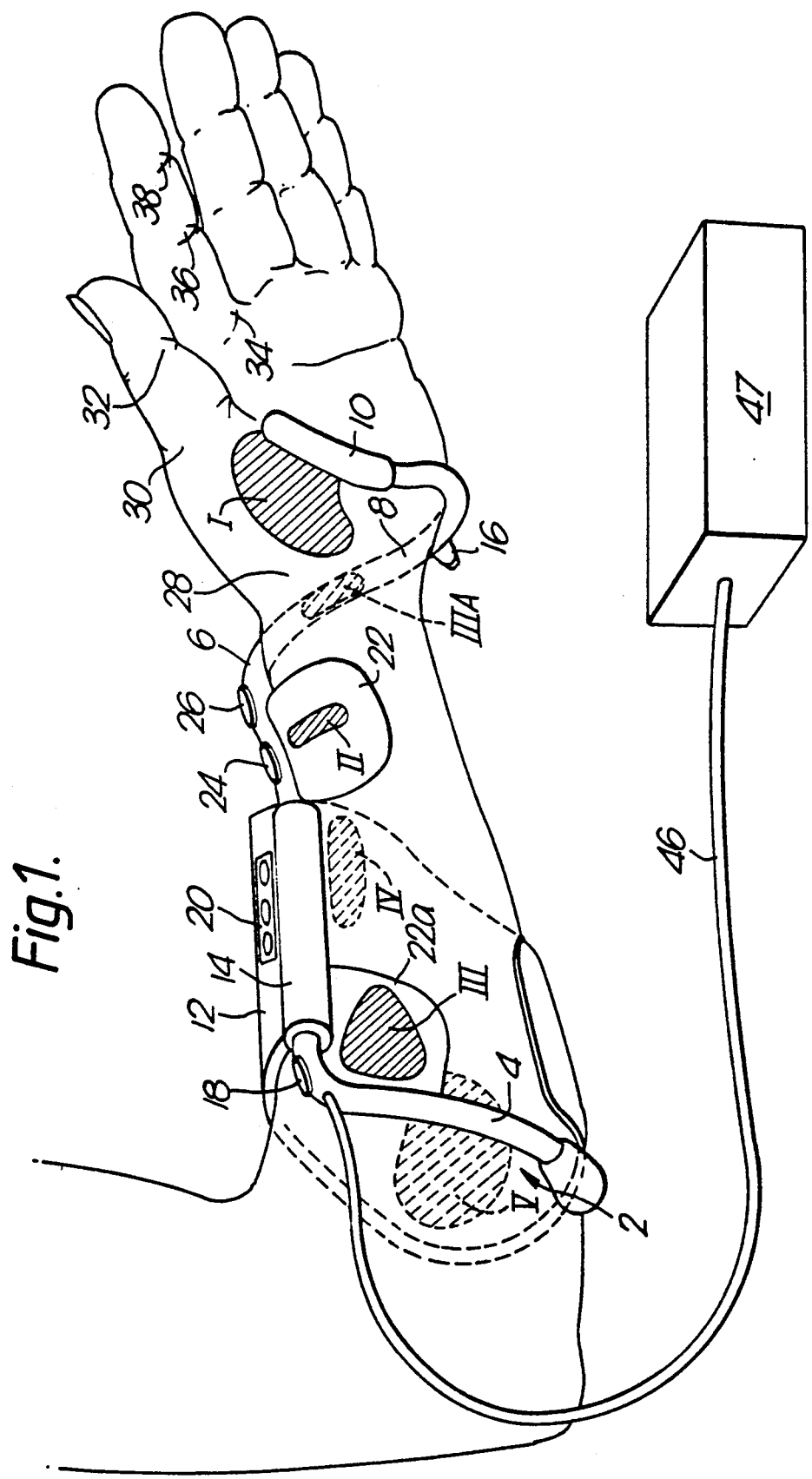
FIG. 1 is a schematic view, in perspective, of a first embodiment of the invention.

Referring now to the drawings, there is seen in FIG. 1 an S-type splint 2 made of a lightweight, but rigid, material such as aluminum tubing, and comprising a forearm portion 4 extending along the palmar side of the forearm; a palmo-dorsal transition portion 6 leading to a dorsal portion 8 extending across the dorsal side of the carpal bones, and a palmar portion 10. This type of splint holds the hand at a fixed angle of wrist extension, which is about 15°.

The splint may be coated with a soft, tough, aesthetic material such as high-density sponge.

To relieve regions of high localized pressure between the splint and the hand, semi-rigid padded plates may be inserted between the splint and the skin. This is particularly applicable to the dorsal surface of the hand, where splint/skin contact pressures are high during hand prehension.

A dorsal flap 12 is attached to the splint 2 by a spring-loaded hinge 14. The flap 12 has two limit positions: an active position as shown in FIG. 1, in which it serves as clamp, pressing the forearm portion 4 of the splint 2 against the palmar side of the forearm (and, by way of reaction, pressing itself against the dorsal side of the forearm); and an open position, defined by a positive stop (not shown) that is part of the hinge 14, to which it can be swung for about 180° and in which it serves as a convenient handle for donning and doffing the device.

The flap 12 may also be held firmly closed against the forearm with a clasp arrangement attached to the tail end of the splint 2.

The flap 12 has additional functions: it carries electrodes IV and V of the five active electrodes, as well as a status display 20, all of which will be discussed further below. It can also be used to accommodate, in its hollow interior, certain components of the electronic circuit as well as operating push buttons or switches.

Further seen are two palmar flaps 22 and 22a, fixedly attached to the forearm portions 4 and 6 of the splint 2, which carries, and presses against the palmar surface of the forearm, electrodes II and III respectively. Electrode I is mounted on the end of the palmar portion 10 of the splint 2.

Push buttons 24, 26 mounted on the palmo-dorsal portion 6 of the splint 2 are used to control stimulation intensity.

In the arrangement shown, Electrode I activates the thenar group of muscles, giving flexion of the carpophalmetacarpophal and metacarpophalangeal thumb joints 28 and 30. Electrode II activates the flexor pollicis longus muscle, giving flexion of the metacarpophalangeal and the interphalangeal thumb joints 30 and 32. Electrode III activates the flexor digitorum superficialis muscle, generating flexion of the finger metacarpophalangeal and proximal interphalangeal joints 34 and 36.

Electrodes IV and V generate opening of the fingers and thumb. Electrode IV activates the extensor digitorum muscle ED, giving extension of the metacarpophalangeal joints 34, and the interphalangeal joints 36 and 38 of the fingers. Electrode IV activates the extensor pollicis brevis muscle EPB primarily. This gives extension of the carpophalmetacarpophalangeal joint 28 and the metacarpophalangeal joint 30 of the thumb. Electrode IV can also, by overflow, activate the abductor pollicis longus muscle APL, producing extension of the metacarpophalangeal joint 28 and the interphalangeal joints 30 and 32, and also the extensor pollicis longus muscle EPL, resulting in extension of the interphalangeal thumb joints 30 and 32.

Other muscles may be activated, for example, the first interossus muscles for generating a pinch grip (in which an object is held between the distal phalanges of the thumb and index finger), the flexor digitorum profundus and the extensor indicis for augmenting finger flexion and extension. The muscles activated by electrodes I to V, however, form the basis of hand function.

The electrodes, which may be allowed to slide across the skin surface during arm articulation, and particularly during forearm pronation/supination movements, can be made of any acceptable conductive material, although conductive silicon rubber was used here. The geometry (shape and size) of the electrode is controlled to fit the curves of the skin surface, to cover the receptive area overlying the target muscle, to allow a balanced current flow to each target muscle which depends on the contact area of the electrode, and to avoid regions of high sensory sensitivity or affect efferent or afferent nerves. A characteristic geometry for each electrode reflects the neuromuscular anatomy underlying the target region. The geometries of electrodes I to V are shown in FIG. 1. Electrode I, for example, is shaped to substantially overlay the flexor pollicis brevis fibres of the thenat group of muscles. It is curved to fit the convex shape of the base of the thumb, while a region at its proximal lower end is removed to avoid stimulating the afferent sensory nerve fibres running along the central palmar region of the hand. During the gripping mode of stimulation, the current is supplied to electrodes I and II and divides approximately in proportion to the relative surface areas of the two electrodes. This area ratio reflects the relative stimulation current requirements of the two target muscles. Electrodes at other stimulation sites each have criteria for defining their controlled geometries.

To ensure electrical contact between the electrode and skin surface, a conductive liquid such as water or a conductive gel may be used. Electrodes may also be covered with a water-absorbing layer. However, gel-filled pouches could be used instead. Conductive gel may be spread over the electrode surface prior to donning the system, or can be supplied through the electrode from a reservoir behind.

Each electrode is attached to the splint 2, first temporarily and, eventually, permanently, within an adjustment area. During fitting of the device to the user, the optimal position of each electrode is located on the limb, the electrodes being temporarily affixed to the splint 2, using an adhesive backing on the electrodes or "Velcro" until the clinician is satisfied with the positioning, after which they are permanently attached, using a cement or other means of fixation.

Leads from each electrode, joined in a cable 46, pass through the tubing of the splint 2 to a microprocessor and the stimulator circuit which can be accommodated, e.g., inside the dorsal flap 12, in the splint tubing itself, or in a separate housing 47 attachable, to a wheelchair or to the patient's upper arm.

The microprocessor allows combinations of two or more electrodes to be active at the same instant. In the configuration shown, two grips are obtainable, as well as a physiotherapy mode, with the microprocessor allowing electrode combinations, stimulation strength (burst width, intensity), phase timing and burst frequency to be custom-programmed to suit the needs of the user.

| a) | Key Grip: | |
|---|---|---|
| | 1) Hand Opening | Electrodes III and IV |
| | 2) Grip | Electrodes I, II and III |
| | 3) Release | Electrodes III and IV |
| b) | Grasp: | |
| | 1) Hand Opening | Electrodes I, IV and V |
| | 2) Grip | Electrodes I, II and III |
| | 3) Release | Electrodes I, IV and V |
| c) | Physiotherapy Mode: | |
| | 1) Hand Extension | Electrodes IV and V |
| | 2) Hand Flexion | Electrodes I, II and III |
| | 3) Hand Extension | Electrodes IV and V |

Each gripping sequence is carried out in three stages. The first stage, hand opening, characterizes the grip. In the grasp grip the fingers are extended and the thumb is abducted, then moved into opposition with the fingers. With this grip, the object is maneuvered into the hand between the open fingers and the thumb. In the key grip, however, the fingers are flexed closed, and the thumb is extended. The object is now maneuvered into the space between the thumb and the lateral edge of the index finger.

The grip itself, stage two, is generated for both the grasp and the key grip, using electrodes I, II and III which activate the flexor muscles. The hand configuration for the grasp and key grip is totally different, however, because the different hand opening configurations cause the object to be grasped differently. Also, the configuration of the hand in gripping is determined by the shape of the gripped object, and where in the hand it is to be held.

Additionally, the shape of the held object can be modified to facilitate gripping: e.g., a sleeve may be placed around a pen to broaden it or to increase its friction coefficient and thus improve the stability of the grip.

The third stage, release, is basically the same as hand opening in reverse. Other grips and hand configurations could be generated, using further combinations of the electrodes shown. By activating additional muscles by additional electrodes, for example, a pinch grip could be generated, the hand may be opened in a flat configuration, or the index finger alone may be extending in a "pointing" hand configuration.

In order to balance the current flow through electrodes I, II and III, and hence the strength of contracting of the underlying muscles, a dummy electrode IIIA may be placed on a neutral area of skin. This serves to channel away some of the stimulation current to a neutral region where it does not activate a muscle, thus reducing the current entering the muscles through electrode III to the same level as that entering the muscles through electrodes I and II. Alternatively, the dummy electrode IIIA may be used as an additional stimulating electrode to supplement the stimulation current activating an already activated muscle or may be used to recruit an additional muscle into operation.

Additionally, a variable resistor is connected in series with each electrode to enable the relative stimulation intensity to be adjusted for each electrode individually. A further variable resistor enables the relative strengths of the two gripping modes to be balanced one against the other. The default level of intensity of stimulation to which the device returns after it is switched off and on is also adjustable by a set of dip switches. The above variable resistors and dip switches are housed on a covered control panel inside the electronic box, and are intended to be adjusted and preset by the prescribing medical clinic only.

A single-channel, constant-voltage stimulator is used together with a microprocessor to carry out switching between electrodes and to control stimulation intensity delivered to each electrode. It would also be possible to use constant-current stimulation, in which constant, current-controlled pulses are passed between the stimulation electrodes ( instead of the constant-voltage-controlled pulses), although this involves the risk of burning the skin, should the electrode-skin contact area diminish.

One of the possibilities would be to provide voltage-controlled biphasic symmetrical square-wave pulses at a frequency of 10 kHz in bursts of approximately 18 Hz, as shown in FIG. 3. The number of pulses in the burst (i.e., the burst width) is the parameter controlling the global stimulation intensity generated. Other stimulation parameters could be used; the stimulation waveform need not be square, and may be monophasic compensated instead of biphasic. A further option is to generate wide single or double pulses instead of pulse bursts and to modulate the voltage intensity instead of the pulse width (FIG. 4). Finally, the frequency of the latter pulses or of the pulse bursts may be modulated to control stimulation intensity.

The system is powered by rechargeable or disposable batteries.

Two push buttons (24, 26) enable the quadriplegic to control the strength of the stimulation: button 24 increases the pulse burst width incrementally by approximately 4%, while button 26 decreases the burst width by the same amount each time it is pressed. Should the device be voltage-intensity controlled, these buttons would increment the voltage intensity.

A control panel is available for adjustment of the device, generally by the clinician. Here a "default" stimulation-intensity control enables setting of the level of stimulation intensity when the device is first switched on. Thereafter, the quadriplegic has control of the level during subsequent operation. Another control allows stimulation intensity to each muscle to be adjusted. Once again, this adjustment would generally be carried out by a clinician on initial fitting of the device. A further control is provided on the panel for adjusting the relative intensities of stimulation between the different gripping modes. Control of timing is provided to enable the clinician to adjust the timing of each phase of operation of the device to suit the needs and skills of the quadriplegic. Finally, control of voltage intensity is provided to enable the clinician to set the overall voltage intensity level to suit the quadriplegic.

A terminal is provided for access by the clinician to store information, such as the total time the equipment has been in use.

In the physiotherapy mode of stimulation, stimulation is switched cyclically between the extension and the flexion electrodes and pulse frequency is reduced to approximately one half of that used for hand articulation modes (i.e., approximately 10 Hz), with interspersed periods of higher frequency stimulation. These parameters could also be made adjustable. Another possible physiotherapy regime is to maintain the stimulation of the flexor muscles to supply active resistance to the extensor muscles, and vice-versa.

Selection of the operating mode is carried out by push button 18. Pressing this button cycles the device through the available modes: in this configuration, from key grip to grasp grip to physiotherapy and back to key grip. Other modes, if included, could be similarly called.

Thin film contact switches or any small light switches, such as micro-switches, may be used. The switches are intended to be operated by the opposite arm of the patient, or by pressing on some convenient object, such as the arm of the wheelchair, the table, or the chin of the quadriplegic. Where it is more convenient, such as where arm articulation is limited, the control switches for the device may be arranged on a separate control panel to be operated by the opposite limb, by the opposite shoulder in a joystick arrangement, or by head movements. Other possibilities for commanding the system include voice activation, operation from e.m.g. signals from independent muscles under voluntary control of the quadriplegic, or by a breath-activated "puff-suck" command interface. A remote control unit can also be used, activating the device with, e.g., infra-red radiation.

Figure 6:
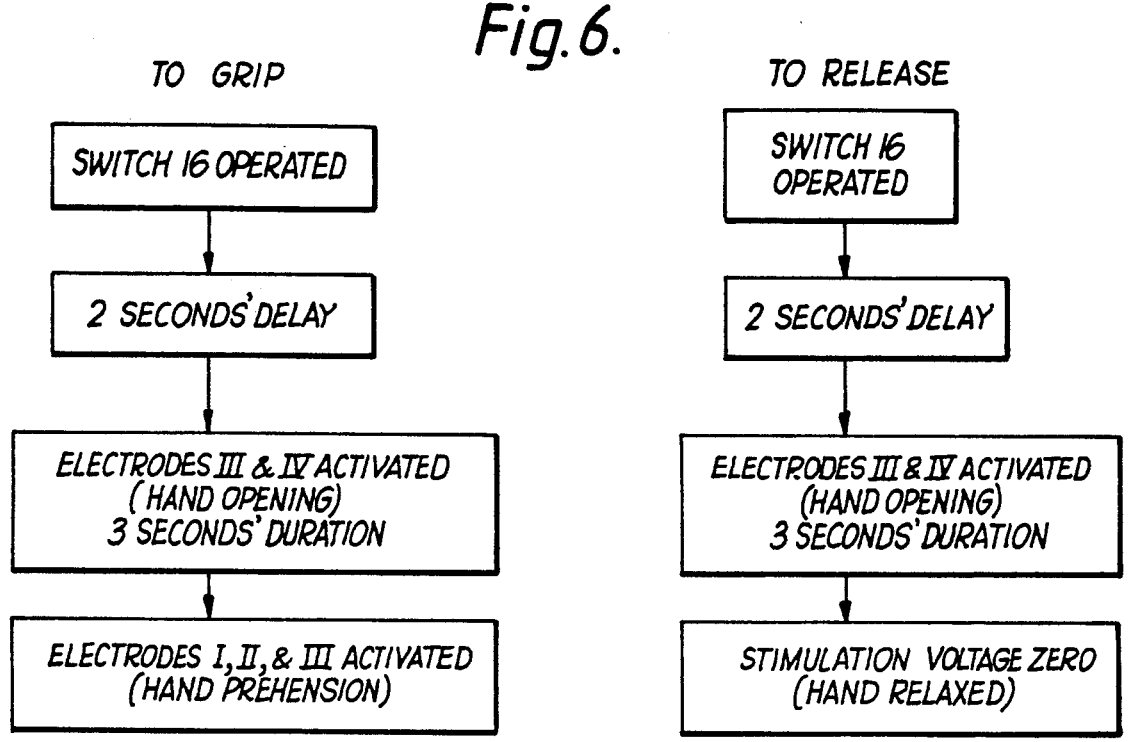
FIG. 6 shows the operational sequence in the key-grip mode.

Switch 16 initiates the hand articulation sequence. Pressing the switch generates about two seconds of delay, followed by approximately 3 seconds of hand opening, followed by hand closing to grip. A further pressing of switch 16 generates another 2-second delay, then causes the hand to open for 3 seconds approximately, after which the stimulation current ceases and the hand relaxes. The time that the hand is in the open state may be adjusted. In the basic arrangement, with switch 18 calling the key grip mode, the sequence is as represented in FIG. 6.

Figure 7:
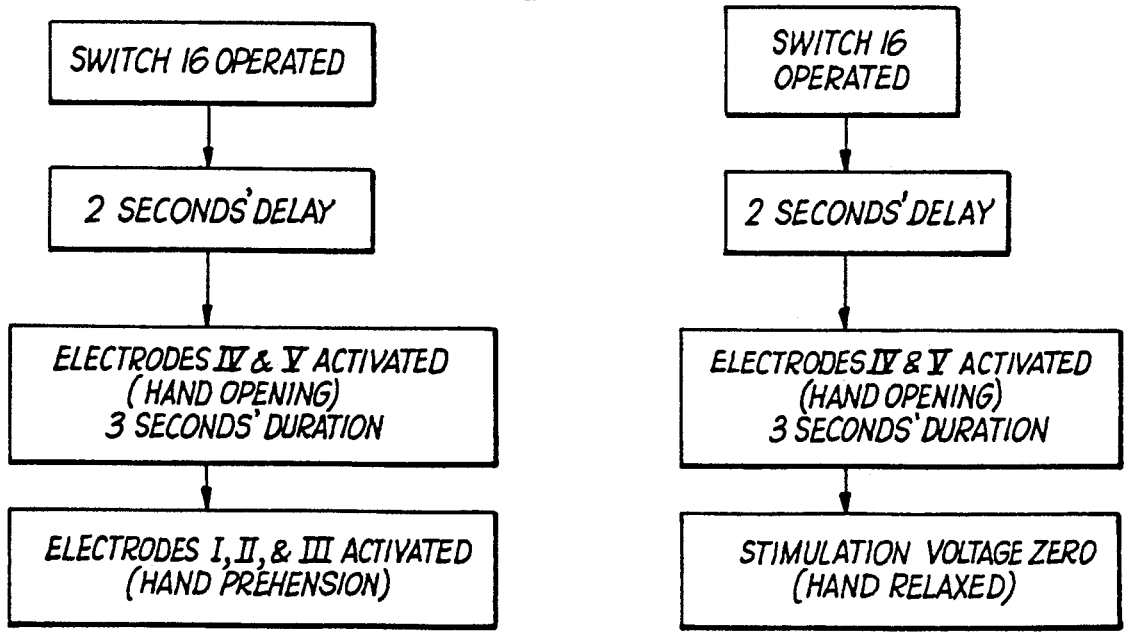
FIG. 7 shows the operational sequence in the grasp-grip mode.

Pressing switch 18 again calls the grasp mode, with the sequence as illustrated in FIG. 7.

Pressing switch 18 once more calls the physiotherapy mode, with the sequence outlined in FIG. 8.

It is obvious that other grips and sequences may be programmed into the system.

While the splint 2 of FIG. 1 holds the wrist joint at a fixed angle of extension, the splint 2 of the embodiment of FIG. 2 allows voluntary or stimulation-generated wrist flexion-extension. At about the palmo-dorsal transition portion 6 (FIG. 1), there is provided a spring-loaded hinge joint 40, whereby the forearm portions 4 and 6 of the splint are articulated to the dorsal- palmar splint portions 8, 10. The joint is spring-based against flexion and has a stop, defining the position of rest of the above dorsal-palmar portion, i.e., of the patient's hand, which is a position of wrist extension of about 15°. Obviously, the pivoting axis of the hinge joint 40 must be in substantial alignment with the natural wrist axis of flexion/extension (no provision being made for abduction, adduction and circumduction). Where sufficient voluntary wrist extension is present (C6/C7 quadriplegia), extending the splint to the hand segment is unnecessary, and a rigid or semi-rigid cuff 39 located against the underlying forearm bones may be used (FIG. 5 ).

Controls are the same as in the embodiments of FIGS. 1 and 2, identical reference numerals denoting identical functions.

The cuff 39 may also be in the form of two hinged sections which close onto the forearm and locate thereon with the help of the underlying bone structure. A flexible spinal cuff may also be used. The splint 2 may be attached by a hinge arrangement of a per se known arm support, where the residual voluntary strength in the upper limb is insufficient to support it against gravity. If wrist flexion-extension is to be stimulation-generated, at least two more electrodes must be provided for the appropriate muscles to be stimulated.

Several outputs are provided from the microprocessor/stimulator unit 47. Both arms could be activated simultaneously, but independently, both using the forearm splint 2 and an upper-arm cuff for activating muscles of the upper arm, such as the triceps brachii.

FIG. 9 shows the upper arm cuff. One electrode pair 41, 42 is attached to the inside of a cuff 44, which is placed around the upper arm. The electrodes are positioned on the lateral posterior surface of the arm at approximately midway along the segment where the motor point of the muscle is located. Here, exact positioning of the electrodes is not required, as the muscle is large and separated from neighboring muscles.

In this embodiment, the cuff 44 itself is made from a semi-rigid plastic material that can be opened and placed on the arm. The flexibility of the cuff itself holds the electrodes firmly on the skin. Other cuff configurations and materials may, however, be used.

Electrical stimulation to the cuff electrodes 41, 42 is controlled independently of the forearm and hand device, although the same microprocessor/stimulator is used to supply and control stimulation through cable 46. The controls comprise a push button on-off switch 48, and a pair of push buttons 50, 52 for incrementally raising and lowering the stimulation intensity, and thus the contraction activity of the muscle, which thereby controls the extension of the elbow joint. The stimulation level may be set to a mid-range intensity and the elbow flexed by voluntary contraction of the (unparalyzed) biceps brachii muscle against the resistance provided by the stimulation-activated triceps brachii. This effectively stabilizes the arm as it is raised up, for example, in lifting a cup to the mouth. Activation of the triceps brachii and the resulting elbow extension generated, increases the vertical reach of the wheelchair-bound user of the device. Finally, when extended at the elbow joint, the arms may be used to provide support or stability to the upper body of the operator by enabling him to push downwards or sideways with his arms on his wheelchair, bed, wall, etc.

The output display 20, either of the LED or the liquid crystal type and conveniently located on the dorsal flap 12 of both embodiments, indicates the status of the device:

a) ON-OFF (A blank field signifies OFF.)
b) Type of grip ( key, grasp, etc. )
c) Stimulation intensity (on a scale of, i.e., 1 to 10)
d) Battery status It will be evident to those skilled in the art that the invention is not limited to the details of the foregoing illustrated embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A device for generating hand function, comprising:
   an S-type splint consisting of a forearm portion adapted to extend along the palmar side of the forearm, a palmo-dorsal transition portion leading to a dorsal portion adapted to extend across the dorsal side of the carpal bones of the hand. and a palmar portion, at least the end of which is adapted to touch the palm of the hand of the wearer of said device;
   a plurality of electrodes, mounted on said splint in positions in which they are adapted to make contact with skin portions directly overlying muscles to be stimulated, said electrodes being connectable to an electronic circuit adapted to produce, upon activation, stimulation currents delivered via combinations of said electrodes in predetermined, timed sequences to preselected groups of muscles, and
   at least one switching means, so located on the device as to be actuatable by the wearer of said device, by which means said predetermined, timed sequences can be initiated.

2. The device as claimed in claim 1, wherein the geometry of said electrodes is selected with respect to surface area, outline and surface curvature so as to be adapted to deliver the required level of stimulation current and to prevent overflow to unwanted muscles or efferent or afferent nerves.

3. The device as claimed in claim 1, further comprising second switching means mounted on the device, for the setting of different gripping modes.

4. The device as claimed in claim 1, further comprising means mounted on the palmo-dorsal transition portion to adjust stimulation intensity.

5. The device as claimed in claim 1, further comprising a spring-loaded dorsal flap hingedly mounted on said forearm portion of said splint, which flap, in the mounted position of said device, is adapted to pull said forearm portion against the palmar surface of the forearm.

6. The device as claimed in claim 5, wherein said flap accommodates at least one of said plurality of electrodes.

7. The device as claimed in claim 6, wherein said flap also accommodates said switching means.

8. The device as claimed in claim 6, wherein said flap also accommodates a source of electric power.

9. The device as claimed in claim 1, further comprising a palmar flap fixedly attached to said forearm portion of said splint, carrying at least one of said plurality of electrodes and, in the mounted position of said device, adapted to press said at least one electrode against the palmar surface of the forearm.

10. The device as claimed in claim 1, wherein at least one of said plurality of electrodes is mounted on the end of said palmar portion of said splint.

11. The device as claimed in claim 1, further comprising a hinge joint interposed between the forearm portion of said splint and the dorsal portion thereof, whereby said dorsal portion and said palmar portion are pivotably articulated to said forearm portion, wherein the pivoting axis of said hinge joint is adapted to be in substantial alignment with the flexion/extension axis of the wrist of the wearer.

12. The device as claimed in claim 11, wherein said hinge joint is spring-biased against flexion, and is provided with stop means defining the position of rest of said dorsal-palmar portion, being a position of wrist extension of about 15°.

13. A device for generating hand function, comprising:
   a cuff donnable on, and adapted to substantially envelop, the forearm;
   a plurality of electrodes, mounted on said cuff in positions in which they are adapted to make contact with skin portions directly overlying muscles to be stimulated, said electrodes being connectable to an electronic circuit adapted to produce, upon activation, stimulation currents delivered via combinations of said electrodes in predetermined, timed sequences to preselected groups of muscles, and
   at least one switching means so located on the device as to be actuatable by the wearer of said device, by which means said predetermined, time sequences can be initiated, wherein said cuff is made of a semi-rigid material having a shape which facilitates clamping of the cuff onto the forearm of the wearer thereof by elastic forces.

14. A device for generating hand function, comprising:
   a cuff donnable on, and adapted to at least partly envelop, the upper arm;
   a plurality of electrodes, mounted on said cuff in positions in which they are adapted to make contact with skin portions directly overlying muscles to be stimulated, said electrodes being connectable to an electronic circuit adapted to produce, upon activation, stimulation currents delivered via combinations of said electrodes in predetermined, time sequences to preselected groups of muscles, and
   at least one switching means, so located on the device as to be actuatable by the wearer of said device, by which means said predetermined, timed sequences can be initiated, wherein said cuff is made of a semi-rigid material having a shape which facilitates clamping of the cuff onto the upper arm of the wearer thereof by elastic forces.

15. A device for generating hand function, comprising:
   a cuff donnable on, and adapted to substantially envelop, the forearm;
   a plurality of electrodes, mounted on said cuff in positions in which they are adapted to make contact with skin portions directly overlying muscles to be stimulated, said electrodes being connectable to an electronic circuit adapted to produce, upon activation, stimulation currents delivered via combinations of said electrodes in predetermined, timed sequences to preselected groups of muscles, and
   at least one switching means so located on the device as to be actuatable by the wearer of said device, by which means said predetermined, timed sequences can be initiated, wherein said cuff is in the form of two hinged, rigid sections adapted to close onto the forearm and be positioned thereon with the help of the underlying bone structure.

* * * * *